(12) United States Patent
Dam (10) Patent No.: US 9,283,315 B2
(45) Date of Patent: Mar. 15, 2016

(54) APPARATUS AND METHOD FOR REAL TIME MEASUREMENT OF A CONSTITUENT OF BLOOD TO MONITOR BLOOD VOLUME

(75) Inventor: Naim Dam, Muttontown, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 490 days.

(21) Appl. No.: 13/022,949

(22) Filed: Feb. 8, 2011

(65) Prior Publication Data

US 2012/0203476 A1  Aug. 9, 2012

(51) Int. Cl.
| | | |
|---|---|---|
| *G01F 1/00* | (2006.01) | |
| *G01F 7/00* | (2006.01) | |
| *A61M 1/36* | (2006.01) | |
| *A61B 5/145* | (2006.01) | |
| *G01N 29/024* | (2006.01) | |
| *G01N 29/22* | (2006.01) | |
| *A61B 5/1455* | (2006.01) | |

(52) U.S. Cl.
CPC ............ *A61M 1/367* (2013.01); *A61B 5/14535* (2013.01); *A61B 5/14557* (2013.01); *G01N 29/024* (2013.01); *G01N 29/222* (2013.01); *A61M 2205/3375* (2013.01); *A61M 2230/207* (2013.01); *G01N 2291/02466* (2013.01)

(58) Field of Classification Search
CPC ..... G01F 1/7082; G01F 1/74; A61B 5/14535; A61M 2205/3375; A61M 2230/207
USPC .......................................................... 702/48
See application file for complete search history.

(56) References Cited

U.S. PATENT DOCUMENTS

| | | | | |
|---|---|---|---|---|
| 5,179,862 | A | | 1/1993 | Lynnworth |
| 5,230,341 | A | | 7/1993 | Polaschegg |
| 5,453,576 | A | | 9/1995 | Krivitski |
| 5,663,503 | A | * | 9/1997 | Dam et al. ...................... 73/649 |
| 5,685,989 | A | | 11/1997 | Krivitski |
| 5,830,365 | A | | 11/1998 | Schneditz |
| 6,029,507 | A | | 2/2000 | Faber |
| 6,122,968 | A | * | 9/2000 | Vandervalk ...................... 73/642 |
| 6,165,151 | A | | 12/2000 | Weiner |
| 6,550,345 | B1 | | 4/2003 | Letton |

(Continued)

FOREIGN PATENT DOCUMENTS

DE  10243069 B4  7/2006

OTHER PUBLICATIONS

"Hematocrit Based Blood Volume Monitoring and the Hemodialysis Patient", 2010, of Hema Metrics, LLC, 695 North, 900 West, Kaysville, UT 84037-4118.

(Continued)

*Primary Examiner* — Michael Nghiem
(74) *Attorney, Agent, or Firm* — Fish & Richardson P.C.

(57) ABSTRACT

Apparatus and method for non-invasively determining the level of a constituent of a patient's blood drawn though an elastomeric tubing to a dialysis machine deforms the tubing in the slot of a measuring head having two points of different transverse length with a transmit/receive sensor at each point that transmits a signal through the tubing and the blood and is reflected back to it from the tubing internal wall. The round trip transit time of the signal at each sensor is measured and the blood sound velocity is calculated from the two round trip transit times and the differential of the transverse lengths at the two points. Blood hematocrit level, which is related to blood volume, is calculated from the calculated sound velocity and an empirical relationship.

4 Claims, 3 Drawing Sheets

(56) References Cited

U.S. PATENT DOCUMENTS

| | | | |
|---|---|---|---|
| 6,821,432 B2 | 11/2004 | Metzner | |
| 7,194,919 B2 * | 3/2007 | Shkarlet et al. | 73/861.18 |
| 7,481,114 B2 | 1/2009 | Lynnworth | |
| 7,608,043 B1 | 10/2009 | Lee et al. | |
| 7,661,294 B2 | 2/2010 | Dam | |
| 7,838,296 B2 | 11/2010 | Corey | |
| 8,694,271 B2 * | 4/2014 | Dam | 702/48 |
| 8,714,017 B2 * | 5/2014 | Dam | A61B 8/00 73/597 |
| 2004/0054283 A1 | 3/2004 | Corey et al. | |
| 2006/0052963 A1 | 3/2006 | Shkarlet | |
| 2006/0287600 A1 * | 12/2006 | McEowen | A61B 5/02007 600/481 |
| 2007/0266778 A1 * | 11/2007 | Corey et al. | 73/61.75 |
| 2011/0009800 A1 * | 1/2011 | Dam | A61M 1/3626 604/6.16 |
| 2012/0143529 A1 * | 6/2012 | Dam | 702/48 |
| 2013/0304403 A1 * | 11/2013 | Dam | 702/48 |

OTHER PUBLICATIONS

J. Lubber and R. Grabber, Ultrasonic Medical Biology, vol. 24, p. 1065 (1998).

Bradley, D. L. and Sacerio, J. L. "The velocity of ultrasound in human blood under varying the physiologic parameters", J. Surg. Res., 12, 290, 1972.

International Search Report mailed May 4, 2012 associated with counterpart International Application No. PCT/US2012/024093.

Sacerio, Jose L., "Determination of Velocity Ultrasonics in Whole Human Blood", 25th ACEMB Americana Hotel, Bar Harbour, FL, Oct. 1-5, 1972.

* cited by examiner

APPARATUS AND METHOD FOR REAL TIME MEASUREMENT OF A CONSTITUENT OF BLOOD TO MONITOR BLOOD VOLUME

FIELD OF THE INVENTION

The present invention relates to an apparatus and method for non-invasively measuring one or more constituents or properties of blood that is flowing in a tubing, such as used with a hemodialysis machine during a dialysis procedure, from which the blood volume of a patient undergoing the procedure can be monitored.

BACKGROUND OF THE INVENTION

Hemodialysis is a process or procedure by which an artificial kidney replaces the function of a patient's kidney. Hemodialysis removes waste products such as creatinine and urea, by circulating blood outside the body through an external filter, called a dialyzer, that contains a semipermeable membrane. The blood flows in one direction and a dialysate flows in the opposite direction across the filter. The countercurrent flow of the blood and dialysate maximizes the concentration gradient of solutes between the blood and dialysate, which helps to remove urea and creatinine from the blood.

Hemodialysis machines perform dialysis by pumping the patient's blood and dialysate through the dialyzer. In the use of such machines, blood is removed from the patient's vascular system via suitable equipment such as an arterial needle, supplied to the machine via a tubing, passed through the machine's dialyzer, and is returned to the patient via a venous needle for normal circulation through the patient's vascular system. Many dialysis patients have an arteriovenous shunt implanted to create a location having a high blood flow that simplifies the withdrawal of blood through a line connected to the part of the shunt that is closer to the arterial side of the shunt and the return of purified blood through a line connected to the shunt downstream of the withdrawal site, closer to venous side of the shunt.

While hemodialysis treatment achieves its desired beneficial effect various physiological parameters are affected during a treatment session which are relevant to cardiovascular stability of the patient undergoing the treatment. The dialysis treatment causes changes in body temperature and osmolarity. Potential problems caused by dialysis include acetate-induced vasodilatation, bio-incompatibility reactions, and malfunctions of the autonomous nervous system. It also has been found that symptomatic hypertension occurs in during a phase of about 20% of all dialysis treatments. This is because stress is placed on the blood pressure control system of the body due to the reduction of blood volume that is caused by ultra-filtration of the blood during the dialysis process. It is generally accepted that blood volume reduction during the dialysis process is an important, and may be even the most significant, factor for triggering the drop of the patient's blood pressure. Therefore, it is highly desirable, to be able to monitor the blood volume of a patient undergoing a dialysis treatment on a real-time basis so that changes in the treatment can be promptly undertaken to avoid and counteract any adverse affects to the patient.

It is generally known that the blood volume of a patient cannot be directly measured as an absolute quantity. Instead, techniques have been developed that give indications of the blood volume based on constituents contained in the blood. One such constituent is the level of hematocrit present in the blood. At page 10 of an article by Diana Hlebovy, "Hematocrit Based Blood Volume Monitoring and the Hemodialysis Patient", 2010, of Henna Metrics, LLC, 695 North, 900 West, Kaysville, Utah 84037-4118 a formula is given that is used to determine the percent blood volume change based on the hematocrit change. Accordingly, it would be desirable to be able to measure is the hematocrit level during a dialysis procedure to provide an indicator of the patient's blood volume. It also would be desirable to accomplish this on a continuous real time basis that is non-invasive, meaning that there is no contact of any part of the measuring apparatus with the blood or the dialysate. It is even more desirable that this be accomplished without the need for additional or changes in the deformable tubing in which the blood circulates during a dialysis treatment The "sound velocity" of blood has been used to measure various constituents and properties of blood. The term "sound velocity" is a recognized shorthand expression describing a characteristic of the speed at which sound waves travel in a medium. The speed of sound varies depending on the medium through which the sound waves pass. Sound velocity often is a parameter used in describing properties of different substances or mediums. Knowing the value of the sound velocity of a particular medium permits different characteristics or properties of the medium to be determined by using various mathematical algorithms.

U.S. Pat. No. 5,453,576 describes an apparatus and method for measuring hemodynamic blood parameters that includes a sound velocity sensor coupled to at least one of an arterial or venous portion of a patient's blood system. The sensor measures the sound velocity of the blood. An indicator medium is injected into the blood system upstream of the sensor to dilute the bloodstream, and the sensor detects the dilution through changes in measured sound velocity. The sound velocity changes are recorded and used to determine blood hemodynamic parameters.

In U.S. Pat. No. 5,685,989 the measurement of blood flow in a dialysis shunt is obtained by injection of an indicator material into a venous line leading from dialysis equipment to a shunt in the arm of the patient. The blood flow in an arterial line leading from the shunt at a location downstream of the venous line to the dialysis machine is monitored by an arterial line sensor for the presence of the indicator material. A detector connected to a sound velocity sensor provides a dilution curve in response to the change of the sound velocity of the blood due to the presence of the indicator material. The blood flow in the shunt is calculated from the area under the dilution curve.

While such apparatus and methods provide useful information about a patient's blood, they are somewhat difficult to use, particularly on a continuous basis. Accordingly, it would be desirable to have a method and apparatus in which a constituent of blood can be monitored on a continuous basis that is simple to use and does not require the use of a diluent.

SUMMARY OF INVENTION

One aspect of the present invention is directed to a method and apparatus that provides accurate and reliable measurement of a constituent of a patient's blood during a dialysis treatment on a real time basis as the infusion of saline or dialysate takes place with such constituent used for giving an indication or being a predictor of the blood volume of the patient undergoing the treatment. In accordance with this aspect of the invention the sound velocity of the blood flowing in a tubing of elastomeric material supplying the blood taken from a patient to the dialysis machine to be purified is measured non-invasively on a real time basis. Elastomeric tubing is of the type that can be deformed or squeezed to change its cross-sectional, or transverse, length.

In a preferred embodiment of the invention the tubing is held in an elongated slot of a measuring head in which the slot has two sections of different known transverse lengths (distances across the slot). When placed in the slot, the elastic tubing is deformed, or squeezed, into a somewhat elliptical shape in the two slot sections to have the different known transverse lengths. One sensor is placed in the measuring head adjacent to the tubing at a point of each slot section. Each sensor transmits signal energy along a respective path though the wall of the tubing and the flowing blood to be reflected from the opposing inner wall back to the sensor. The round-trip transit time of the signal energy transmitted from and reflected back to each sensor is measured. This is sometimes referred to as a pulse echo measurement. The two round trip transit times will be different because of the different outer transverse lengths of the deformed tubing at the two points of the slot along the tubing length where the sensors are located. The sound velocity of the blood flowing in the tubing is calculated from the differential value of the two transverse lengths, known from construction of the slot or from measurement, and the values of the two round trip measured transit times.

The measuring head also has a sensor that non-invasively measures the temperature of the liquid flowing in the tubing. In a preferred embodiment, it also has a sensor for detecting whether blood or a clear liquid, such as saline solution, is flowing in the tubing. The apparatus includes a microprocessor that controls the transmission and reception of the signal energy, measures the two round-trip transit times and is provided with the differential distance between the two sensors so as to be able to calculate the sound velocity of the flowing blood. The microprocessor further calculates the hematocrit level in the blood from the value of the sound velocity and the measured temperature based on an algorithm programmed in or otherwise available to the microprocessor.

The level of the blood hematocrit constituent is related to the blood volume. Essentially, as the level of the hematocrit constituent decreases, the blood volume of the patient also is decreasing and vice versa. Accordingly, by monitoring the hematocrit level the blood volume of the patient also is being monitored.

Another aspect of the invention provides a non-invasive method and apparatus to determine blood hemodynamic parameters during a dialysis treatment that is easy to use and does not require injection of a diluent or marker into the blood undergoing the dialysis procedure. It also operates on a continuous and essentially real-time basis so that there can be real-time monitoring of the patient's blood volume status during a dialysis treatment session.

The apparatus and method of this aspect of the invention also has the capability of determining the relative blood volume, this being the ratio of the current blood volume to the blood volume at the beginning of the dialysis treatment, or during any other time of the treatment.

BRIEF DESCRIPTION OF DRAWINGS

Other objects and advantages of the present invention will become more apparent upon reference to the following specification and annexed drawings, in which:

FIG. 1 is a diagrammatic representation of a dialysis machine including the apparatus of the invention;

FIG. 2 is a plan view of a piece of tubing having two sections of different transverse (cross-sectional) length used to describe one aspect of the invention;

FIGS. 2A and 2B are end views of the tubing of FIG. 2; and

DETAILED DESCRIPTION OF THE INVENTION

FIG. 1, shows a typical blood dialysis machine 100 having the usual pump 101 and filter 103. The system 100 is shown used with a connection of arterial and venous lines to a blood vessel 112 of a patient 130 undergoing dialysis treatment. The connection illustratively is shown as an arteriovenous shunt connected at its upstream end 114 to the patient's artery 116 and connected at its downstream end 118 to a patient's blood vein 120. The shunt may be an artificial vessel or a native vessel that is surgically moved between artery 116 and vein 120. The direction of flow of blood in the vessel 112 is indicated by arrow 122 and it is this blood flow from with blood volume is to be determined.

Connected between vessel 112 and the blood dialysis machine 100 is an arterial line, such as a tubing 126 of a deformable elastomeric material, having an inlet 128 in the shunt 112 for the pump 101 to draw blood from the patient for treatment by the filter 103 of the dialysis machine. The direction of the blood flow in the tubing 126 is shown by the arrow 127. As the blood is drawn, it passes through a measuring module 140, described in detail below, that measures the sound velocity of a signal through the blood and from this computes various hemodynamic parameters, such as the blood volume. Also connected between the dialysis equipment 100 and shunt 112 is a venous line, or tubing, 132 which carries treated blood from the dialysis equipment 100 back to the shunt. The venous line 132 has an outlet 134 located in shunt 112 downstream of the arterial line 126 inlet 128. The direction of flow of treated blood in venous line 132 is illustrated by arrow 136. Arrow 138 shows treated blood from the venous line tubing outlet 134 traveling downstream in the veins of the patient.

The measurement module 140 uses a pulse echo technique to measure the sound velocity of the blood in the elastomeric deformable tubing 126. Referring to FIG. 2, tubing 126 of an elastomeric deformable plastic material in which the blood is flowing is illustratively shown having two sections 126A and 126B of different transverse length. The tubing material can be of different types such as silicon, Teflon, PVC or any other suitable elastomeric plastic material. The tubing piece of FIG. 2 is part of a longer piece (not shown) that has been deformed, or "squeezed", along the lengths of the two sections 126A and 126B to be somewhat elliptical, as shown by the views of FIGS. 2A and 2B. The tubing deformation, or squeezing, takes place for example when the tubing is placed in a slot of a measuring head in which the slot transverse length is less than the normal circular, or square or rectangular, elastic tubing outer diameter. The tubing typically is squeezed by an amount of from about 10% to 30% of its original outer cross-sectional length although it could be less or more.

The deformed tubing first section 126A is shown as having an outer transverse length LA and an inner transverse length La. The second tubing section 126B, has been deformed by a greater amount to have smaller outer and inner transverse lengths LB and Lb. In each section the wall thickness of the tubing is Lw (LA−La and LB−Lb) and does not change when the tubing is deformed.

Figure 3:
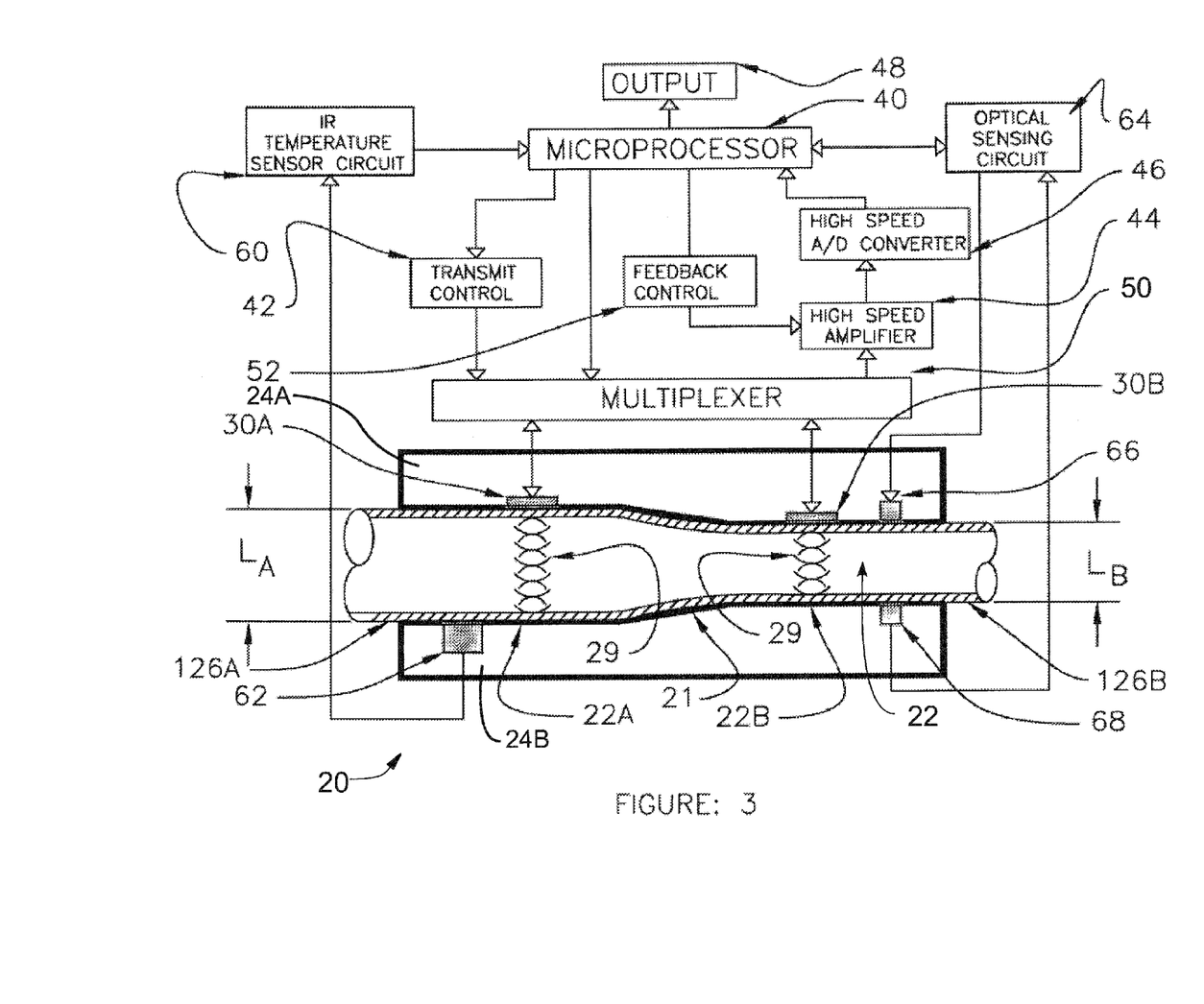
FIG. 3 is a top plan view of an embodiment using the measuring head and associated circuits.

FIG. 3 shows a pre-molded or machined measuring head 20 which can be of any suitable material, such as plastic, that is a part of the measurement module 140. The measurement module can be mounted as part of the machine 100 or be separate from it. Alternatively, the measuring head 20 can be separate from the machine and connected to electronic components mounted in the machine. The head 20 has a continuous slot 22 along its length formed by a bottom wall and two spaced opposing side walls. The slot has a first section 22A having a known transverse length (distance across the slot between the slot side walls 24A, 24B) that tapers down in a transition section 21 to a second slot section 22B having a known smaller known transverse length than that of section 22A. When a piece of the elastic tubing 126 having an outer diameter greater than any transverse length of any part of the slot 22 is placed in the slot it will be deformed to have outer transverse lengths LA and LB that are those of the slot sections 22A and 22B. These transverse lengths correspond to the transverse lengths of the two tubing sections 126A and 126B shown in FIG. 2.

The transverse length of the slot first section 22A is effectively the outer transverse length LA of the first tubing section 126A and the transverse length of the second slot section 22B is effectively the outer transverse length LB of the second tubing section 126B. That is, when the part of the tubing 126 in which the blood is flowing to the dialysis machine is placed in the measuring head slot 22 it assumes dimensions LA, La, LB and Lb that depend on the transverse lengths of the slot 22 at the two slot sections 22A and 22B. The tubing wall thickness Lw does not change at any place where it is deformed. The transverse lengths of the slots of the two sections 22A and 22B are known and fixed. Therefore, the tubing transverse length dimensions LA and LB are known as is the differential dimension LA−LB. Also, $$La = LA - 2Lw \text{ and } Lb = LB - 2Lw.$$

A respective ultrasonic transmit/receive transducer, or sensor, 30A and 30B is mounted in the head 20 in a side wall of each of the slot sections 22A and 22B. Each sensor has a face that is close to the face of the slot wall. Since the tubing in the slot is squeezed, it effectively bonds to the face of the wall whose material serves as a coupling medium to convey ultrasonic energy to and from the sensor. The sensor 30 can be of any suitable piezoelectric material such as PZT (lead zirconate titanate) or PVDF (PolyVinyliDene Fluoride). The face of each sensor 30 is generally parallel to the outer and inner walls of the tubing in the two slot sections and to the blood fluid flowing in the tubing. Each sensor transmits signal energy generally transverse to the tubing longitudinal axis and it is reflected back to the sensor as shown by the arrows 29. The measuring head 20 also has a temperature sensor 62, preferably of the infra-red type that non-invasively measures the temperature of the liquid flowing in the tubing. Further, there preferably is an optical sensor formed by a light source 66, such as an LED, and a photodetector 68. The construction and operation of the temperature sensor 62 and optical sensor are described in U.S. Pat. No. 7,661,294, granted Feb. 16, 2010, the disclosure of which is incorporated by reference herein.

The electronic components of the measuring module 140 include a microprocessor 40 of conventional construction, preferably with an internal memory. The microprocessor is suitably programmed to perform the functions and calculations described below. The microprocessor has an output 48 which can be of any conventional type, such as a digital readout, video display, or any other suitable apparatus for displaying the results of its measurements and calculations. The microprocessor 40 controls a transmit control circuit 42 which provides electrical signals to each of the sensors 30A and 30B. The transmit control circuit 42 includes either a suitable source of the signals that runs continuously and whose output is gated to the sensors 30 to provide bursts of the signals or a generator that the microprocessor activates for the times of the bursts. The microprocessor 40 also operates a multiplexer 50 that controls transmission and reception of the signals by the sensors 30A and 30B.

The electrical signals provided to each sensor 30 are converted into electro-mechanical energy that is transmitted by the sensor. This energy passes generally transversely through the tubing outer wall and the flowing fluid and is reflected from the tubing internal wall opposing the sensor back through the flowing fluid and the tubing outer wall to the same sensor. The sensor then converts the received reflected electro-mechanical energy back to an electrical signal.

Microprocessor 40 also operates to control reception of the reflected energy. That is, there is a pause between the transmission of each burst of signals by a sensor to allow for reception of the reflected energy and the calculation of the round-trip transit time before the next signal burst is transmitted. A high speed amplifier 44 receives the electrical signal from each sensor 30A and 30B of the energy reflected from the internal wall of the tubing at each slot section 22A and 22B. The output of amplifier 44 is applied to a high speed analog/digital (A/D) converter 46 to be converted to digital form. A feedback control circuit 52 is provided to normalize the amplitude of the received signals at the output of amplifier 44 to a fixed value and thereby normalize the amplitude of the output of the A/D converter 46 digital signals that are applied to the microprocessor 40. The microprocessor also receives digital signal inputs from an IR temperature sensor circuit 60 to which the measuring head temperature sensor 62 is connected and from an optical sensing circuit 64 to which the measuring head optical components 66 and 68 are connected.

In making the round trip transit time measurements, the time of transmission of the energy by each sensor 30 is known by the microprocessor 40 since it controls this time. The microprocessor also knows the time of reception of the reflected signals as supplied by the A/D converter 46. Therefore, the microprocessor can calculate the round trip transit time of the signals transmitted from each sensor 30 and received back to it after reflection from the tubing opposing inner wall.

Two round-trip transit values are measured of the signals in the tubing in the slot sections 22A and 22B. These times are different because the transverse lengths of the tubing at each of the slot sections 20A and 20B are different. The circuit preferably operates so that the two round-trip transit times are measured sequentially or at substantially the same time. In a preferred embodiment of the invention, the two transit times are measured as close to simultaneously as possible so that any change in the temperature of the fluid flowing in the tubing 126 between the two slot sections 22A and 22B will not adversely affect the accuracy of the measurements and the final calculation of the sound velocity.

By knowing the two round-trip transit times and the transverse length differential, the sound velocity of the fluid flowing in the tubing 126 can be calculated by the microprocessor. This is explained below.

The tubing transverse lengths LA and LB can be written as:

$$LA = 2Lw + La \tag{1}$$

and $$LB = 2Lw + Lb \tag{2}$$

where,

Lw=wall thickness of a given tubing. This does not change at the points of the tubing squeeze, La=tubing inner transverse length after squeeze at slot section 22A at which sensor 30A is located, and Lb=tubing inner transverse length after squeeze at sensor 30B location.
Therefore, $$LA-LB=La-Lb=Lab \quad (3)$$

where,
Lab=fixed differential of the tubing transverse lengths at the locations of sensors 30A and 30B. Lab is known from the cross-sectional lengths LA and LB of the measuring head slot sections. These are set during manufacture of the head or are directly measured. The differential value Lab is programmed into the microprocessor for use in calculating the sound velocity.

Using the pulse echo technique with a single sensor 30 at each slot section 22A and 22B, the respective round trip travel time ta and tb of the energy at each sensor location 22A and 22B is determined as follows:

$$ta = 2tw + \frac{2La}{V} \quad (4)$$

$$tb = 2tw + \frac{2Lb}{V} \quad (5)$$

where V is the sound velocity of the blood.
From equations (4) and (5), $$ta - tb = \frac{2(La - Lb)}{V} = \frac{2Lab}{V} \quad (6)$$

so that, $$V = \frac{2Lab}{ta - tb} \quad (7)$$

Let: ta−tb=tab, so that $$V = \frac{2Lab}{tab} \quad (8)$$

Thus, by knowing the fixed differential Lab of the tubing internal transverse lengths at the points of each of the sensors 30A and 30B, known from LA and LB as set by the transverse lengths of the measuring head slot sections 22A and 22B, and calculating from equations (1) and (2), and measuring the differential elapsed time tab, the sound velocity V of the flowing blood is accurately calculated independent of tubing wall thickness Lw.

Typical parameters for the instrument by way of example are:
  a. material of tubing—PVC, Teflon, any plastic materials
  b. outside diameter of tubing before squeeze—⅛" minimum to 1" maximum.
  c. wall thickness of tubing 0.01" to 0.1"maximum
  d. tubing inner and outer transverse lengths after squeeze—, approximately 20% to 30% less than before, the squeeze. The tubing wall thickness Lw does not change after the squeeze.
  e. distance between the two sensors 30A and 30B—minimum 0.5", maximum 2.0" length across the slot at each of the two sections 22A and 22B—different for each tubing
  g. length of slot 22—0.5 to 2 inches
  h. operating frequency—2 MHZ minimum—20 MHZ maximum, depends on resolution of system that is desired
  I. duration of pulse bursts of the ultrasonic energy. Minimum 100 nano seconds, Maximum 1 microsecond
  j. time between the bursts—10 microseconds minimum to 5 milliseconds maximum
Other frequencies, burst durations and burst timing as well as other physical dimensions can be used depending on the material and size of the tubing and the accuracy of the result needed.

By knowing the sound velocity V of the blood flowing in tubing 126 and utilizing algorithms that are programmed into the microprocessor or available to it from a separate memory, various hemodynamic parameters of the blood can be determined. One such parameter, the blood hematocrit level, is calculated by the microprocessor using an empirical relationship between the measured sound velocity and the blood hematocrit value such as:

$$Vc=1499.46+0.887HCT \quad (9)$$

where,
  HCT=hematocrit level in percentage
  Vc=blood sound velocity as determined by equation (8) corrected according to a temperature reference model. See, J. Lubber and R. Grabber, Ultrasonic Medical Biology, vol 24, page 1065 (1998).

Equation (9) and the temperature model are programmed into the microprocessor for execution with the temperature being measured by the temperature sensor 60 of the measuring head 20.

By repeating the measurements and calculations of equations (4) through (9) under control of the microprocessor the HCT level can be determined on a real time continuous basis. This effectively can be used to monitor or be a predictor of the patient's blood volume. The apparatus can be provided with various displays to show the HCT levels as they are calculated at different times as well as alarms when the HCT level drops below or exceeds a preset level or when a change exceeding a predetermined level occurs over a preset time interval.

The method and apparatus of the invention also operates to provide an indicator of a predictor of the relative change in the blood volume during any time of the dialysis procedure. To do this, a base hematocrit level is calculated as per equation (10) at a time such as the beginning of the dialysis treatment and before any of the blood has been provided to the dialysis machine, or at some other time during the treatment. This gives a base level HCT(o). The hematocrit level is again determined at a later time to give a level HCT(t). To determine the relative change, the following algorithm (see Steuer et al, cited above at page M92) is performed by the microprocessor:

$$RBV = \frac{BV}{BV(o)} - 1 = \frac{HCT(o)}{HCT(t)} - 1 \quad (10)$$

where:
  RBV: relative change in blood volume.
  HCT(o): base hematocrit level
  HCT(t): hematocrit level at time t during treatment
  BV(o): initial blood volume
  BV(t): blood volume at time t during treatment The blood total protein concentration (TPC) also can be calculated at any time during the procedure using the following algorithm (see Sacario, "Determination of Velocity ultrasonics in whole human blood", 25$^{th}$ Annu. Conf. Eng, Med. Biol., Alliance for Engineering in Medicine and Biology, Bethesda, Md., October 1972, page 39; Bradley, D. L. and Sacerio, J. L. "The velocity of ultrasound in human blood under varying the physiologic parameters", J. Surg. Res., 12, 290, 1972). The TPC value would be programmed into the microprocessor.

$$V=1482.26+1.54T+0.51HCT+2.8TPC \quad (11)$$

where
- V: blood sound velocity as per equation (8)
- T: temperature measured in centigrade.
- HCT: hematocrit as per equation (9)
- TPC: Total Protein Concentration.

A typical dialysis procedure in accordance with the invention proceeds as follows. The procedure is conducted so that there is always a positive arterial pressure during priming of the line set and subsequent circulation of saline solution. The temperature of dialysate, such as saline solution, is set to 37° C.±0.5° C. The saline solution is allowed to circulate to stabilize the temperature which is measured by infrared sensor 62 and its circuit 60. After stabilization of liquid temperature, the dialysis machine is operated for a time of about 6-8 minutes to circulate blood at the correct temperature. The optical sensor 66, 68 and its circuit 64 determines whether the liquid flowing in the tubing is saline solution or blood. The optical sensor determines the color of the fluid flowing in the tube without physically contacting the fluid.

After the optical sensor detects that blood is flowing in the tubing, the dialysis machine is run for a predetermined time, preferably at least 5 minutes, before the ultrasonic sensors 30 start measuring the liquid sound velocity and computing the blood volume. Initial relative blood volume is considered 100% which may reduce to 80%±5% on completion of dialysis treatment.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. Apparatus for measurement of a blood volume related constituent of blood of a patient undergoing dialysis comprising:
    a dialysis machine including a pump and a filter;
    an elastomeric tubing in which blood flows from the patient to said dialysis machine as drawn by said pump;
    a measuring head having an elongated slot with walls between which said tubing is placed to be held, said slot walls having a transverse length along a longitudinal length of said slot, said tubing being deformed in said slot, and said slot having first and second points of different fixed transverse lengths spaced apart along said slot longitudinal length;
    respective first and second ultrasonic transmit/receive sensors, mounted in said measuring head adjacent said slot first and second points, said first and second sensors configured to transmit ultrasonic signal energy along a respective path through a wall of said tubing and the blood flowing therein and receiving the ultrasonic signal energy reflected from an internal wall of said tubing;
    a temperature sensor mounted to said head for measuring a temperature of the blood flowing in said tubing without contacting the flowing blood; and
    a circuit comprising a microprocessor, the circuit for:
        measuring, for each of said first and second sensors, a round-trip transit time of the ultrasonic signal energy from a time of transmission of the signal energy to a time of reception of the signal energy after reflection of the signal energy from said tubing internal wall, and
        calculating the blood volume related constituent of the blood, comprising calculating a blood hematocrit constituent level of the blood, including
            calculating a sound velocity of the blood flowing in the tubing from the measured round-trip transit times and a differential of said fixed slot transverse lengths at said first and second points, and
            calculating the blood hematocrit constituent level based on the calculated sound velocity and the temperature measured by said temperature sensor,
    wherein said microprocessor is for measuring said round-trip transit times, said microprocessor programmed with the value of the differential of the fixed transverse lengths of said first and second points of said slot to calculate the sound velocity of the flowing blood, and an algorithm to calculate the blood hematocrit constituent level,
    wherein said microprocessor operates to calculate the sound velocity V of the blood flowing in the tubing according to:

$$V = \frac{2LAB}{tab}$$

where:
- LAB=the differential of the fixed slot transverse lengths at the two points of said slot, and
- tab=a differential of the two round-trip time measurements, wherein said algorithm for calculating the hematocrit constituent level is:

$$V_c = 1499.46 + 0.887 HCT$$

where:
- HCT=hematocrit level in percentage, and
- $V_c$=corrected blood sound velocity based on the measured temperature.

2. The apparatus as claimed in claim 1 wherein said microprocessor controls time of transmission of the signal energy by said first and second sensors.

3. The apparatus as claimed in claim 1 further comprising an optical sensor mounted to said measuring head to determine a color of the blood flowing in the tubing without contacting the blood.

4. A method of determining a level of a constituent of blood related to a blood volume of a patient undergoing a dialysis treatment comprising the steps of:
    deforming elastomeric tubing via which blood is drawn from the patient to a dialysis machine by placing the elastomeric tubing into a slot having a bottom wall and two opposing side walls, wherein the slot has at two points along a longitudinal length of the slot, different fixed transverse lengths between said opposing side walls, such that the elastomeric tubing contacts the opposing side walls at the two points of different fixed transverse lengths;
    positioning an ultrasonic transmit/receive sensor at each of said first and second points, adjacent and external to said tubing and transmitting ultrasonic signal energy from said ultrasonic sensors in a direction transverse to said tubing, the ultrasonic signal energy transmitted through a wall of said tubing adjacent to each of said ultrasonic sensors and through the blood flowing in the tubing;

receiving the ultrasonic signal energy reflected from a surface of an internal wall of the inside diameter of the tubing opposing each of said ultrasonic sensors;

measuring for each ultrasonic sensor a round-trip transit time of the ultrasonic signal energy from time of transmission of the ultrasonic signal energy to a time of reception after reflection of the ultrasonic signal energy from the opposing internal wall of said tubing;

measuring a temperature of the blood flowing in said tubing without physically contacting said tubing; and calculating the level of a blood constituent related to the blood volume based on a sound velocity of the blood from the measured round-trip times at the two points and a value of the differential of the fixed transverse lengths of said first and second points, wherein said sound velocity is calculated according to:

$$V = \frac{2LAB}{tab}$$

where:
LAB=the differential of the fixed transverse lengths at the two points, and
tab=a differential of the two round-trip time measurements;

correcting the sound velocity based on the measured temperature according to a temperature reference model;

calculating a blood hematocrit level based on the sound velocity according to:

$$V_c = 1499.46 + 0.887 HCT$$

where:
HCT=hematocrit level in percentage, and
$V_c$=corrected blood sound velocity based on the measured temperature.

* * * * *